United States Patent
Bartsch et al.

(10) Patent No.: US 6,558,388 B1
(45) Date of Patent: May 6, 2003

(54) INTRAMEDULLARY NAIL FOR THE HUMERUS

(75) Inventors: Eric Bartsch, Baar (CH); Maja Bürgi, Pfyn (CH)

(73) Assignee: Sulzer Orthopedics Ltd., Baar (CH)

(*) Notice: Subject to any disclaimer, the term of this patent is extended or adjusted under 35 U.S.C. 154(b) by 251 days.

(21) Appl. No.: 09/643,631

(22) Filed: Aug. 22, 2000

(30) Foreign Application Priority Data

Aug. 30, 1999 (EP) ............................................. 99810778

(51) Int. Cl.⁷ ................................................. A61B 17/56
(52) U.S. Cl. ............................................ 606/62; 606/67
(58) Field of Search ............................ 606/62–64, 68, 606/67

(56) References Cited

U.S. PATENT DOCUMENTS

| | | | |
|---|---|---|---|
| 2,327,434 A | * 8/1943 | Johnston | |
| 2,998,007 A | 8/1961 | Herzog | |
| 3,791,380 A | 2/1974 | Dawidowski | |
| 4,204,531 A | * 5/1980 | Aginsky | |
| 4,275,717 A | 6/1981 | Bolesky | |
| 4,519,100 A | * 5/1985 | Wills et al. | |
| 4,632,101 A | * 12/1986 | Freedland | |
| 4,862,883 A | * 9/1989 | Freeland | |
| 5,057,103 A | * 10/1991 | Davis | 606/63 |
| 5,281,225 A | * 1/1994 | Vicenzi | 606/62 |
| 5,534,004 A | * 7/1996 | Santangelo | 606/68 |
| 5,810,820 A | 9/1998 | Santori | 606/63 |
| 5,849,004 A | * 12/1998 | Bramlet | 606/232 |
| 5,971,986 A | * 10/1999 | Santori et al. | 606/62 |
| 6,077,264 A | * 6/2000 | Chemello | 606/67 |

FOREIGN PATENT DOCUMENTS

| | | |
|---|---|---|
| DE | 3413690 A1 | 10/1985 |
| DE | 4210801 A1 | 11/1992 |
| DE | 19707420 A1 | 8/1998 |
| DE | 19615103 C2 | 4/1999 |
| EP | 0064724 A2 | 11/1982 |
| EP | 0517435 A1 | 12/1992 |
| EP | 0561295 A1 | 9/1993 |
| EP | 0738502 A2 | 10/1996 |
| EP | 0882431 A1 | 12/1998 |
| FR | 2727304 | 5/1996 |
| FR | 2747911 | 10/1997 |

OTHER PUBLICATIONS

DEPAnet—Bibliographische Daten & EP0561295, B1, Abstract.
DEPAnet—Bibliographische Daten & DE3413690, Abstract.
DEPAnet—Bibliographische Daten & FR2727304, Abstract.
DEPAnet—Bibliographische Daten & FR2747911, Abstract.
DEPAnet—Bibliographische Daten & DE4210801, Abstract.
DEPAnet—Bibliographische Daten & DE19707420, Abstract.
DEPAnet—Bibliographische Daten & DE19615103, Abstract.

* cited by examiner

*Primary Examiner*—Ralph A. Lewis
(74) *Attorney, Agent, or Firm*—Townsend and Townsend and Crew LLP

(57) ABSTRACT

With the invention a intramedullary nail preferably for the humerus is shown which comprises a securing head for a hammering-in and aiming device, with the intramedullary nail having at least one transverse bore (2) adjoining at the securing head (1), and which comprises an entry tip in the vicinity of which anchoring elements can be extended radially. The anchoring elements are combined in a claw (5) of curved wires (6), with the wires being elastically deformed inside the intramedullary nail in a not outwardly moved state and springing out radially with an axial forwarding of the claw and assuming their original curved shape.

13 Claims, 3 Drawing Sheets

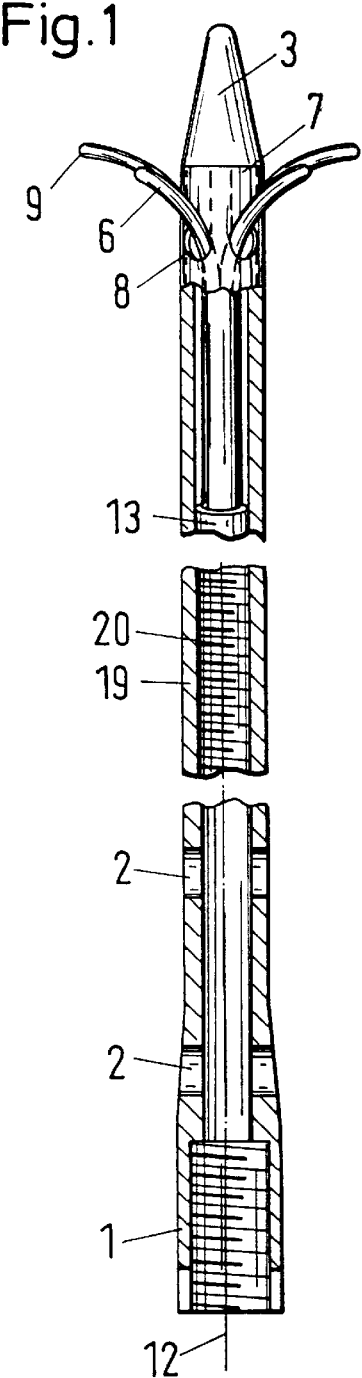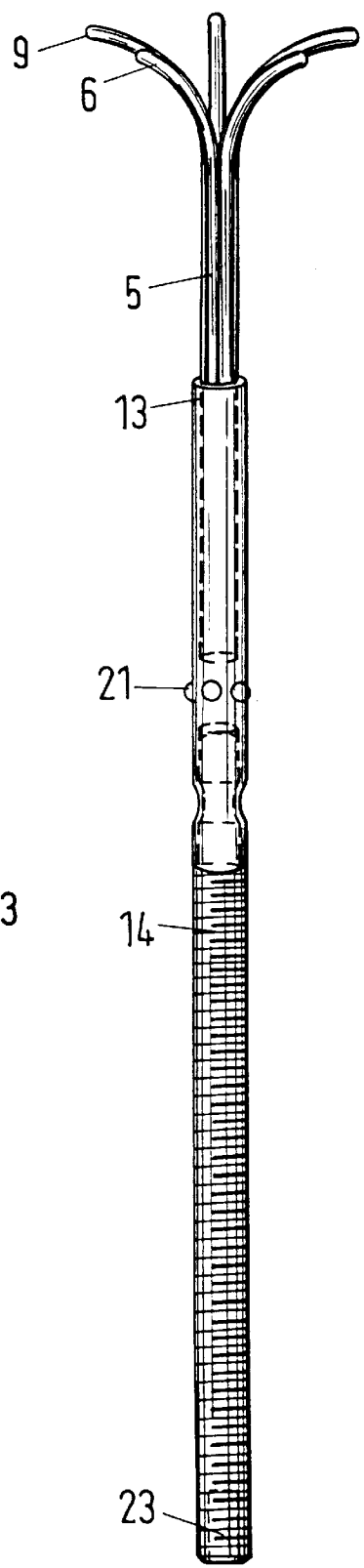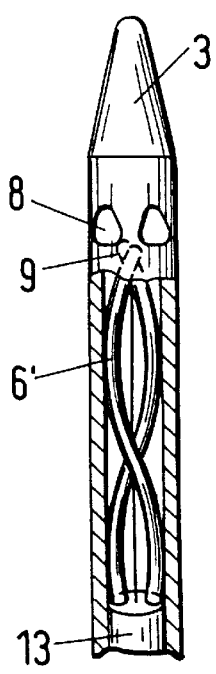

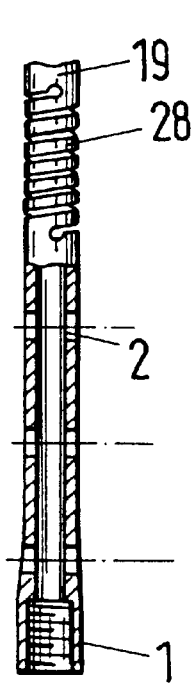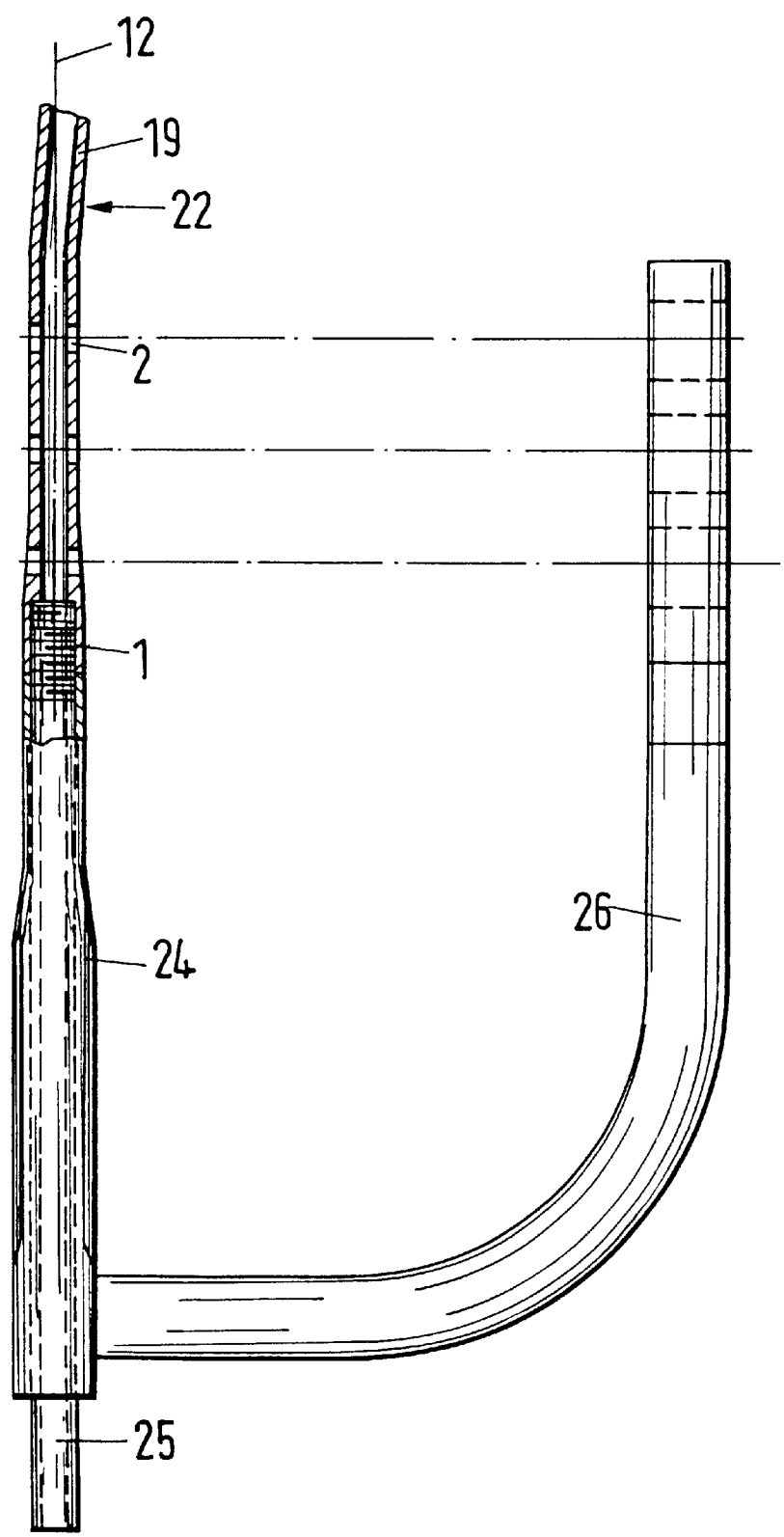

INTRAMEDULLARY NAIL FOR THE HUMERUS

BACKGROUND OF THE INVENTION

The invention relates to an intramedullary nail, preferably for the humerus, comprising a securing head for a hammering-in and aiming device, with the intramedullary nail having at least one transverse bore adjoining at the e securing head, and comprising an entry tip in the vicinity of which anchoring elements can be extended radially.

The intramedullary nailing per se is a gentle method for the operative treatment of fractures of long tubular bones. Important advantages consist in a very small access without scarring worthy of mention and in a closed setting of the fracture. In order to obtain a stable and rotationally secure intra-medullary fracture splinting, intramedullary nails are locked in the bone at both ends by means of pins or screws.

In the treatment of upper arm fractures this locking at the introduction location (near the insertion) is carried out with the help of an aiming bow which is secured at the end of the nail and which at the same time serves as a hand grip for the better introducibility of the intramedullary nail. In it, guides for the borer are provided, which can thus exactly encounter the holes from the outside which are present in the implant. Due to their small diameters a problem exists in almost all humerus intramedullary nails in a locking at the end which is remote from the insertion. Since a finding of remote implant holes with a long aiming device is very complicated and since the nail bends and twists over the length of the entire humerus, the insertion-remote locking takes place freehand under X-ray amplifier translumination. In this an existing hole which is about 4 mm in size must be sought in the implant from the outside and encountered with the borer, which is accompanied by radiation exposure and a high consumption of time.

Intramedullary nails with radially extendable anchoring elements in the vicinity of the entry tip are shown in U.S. Pat. No. 5,810,820. Radially emerging wire tips bore into the bone matter and provide a hold in the axial direction. The wires, which are provided with tips, have a cylindrical shape and are in each case seated in guides in the drawn-in state. The principle of the radial emergence is based on the wires being pressed through axial forwarding into a radial deflection in such a manner that they deform plastically. Through axial restoring the wires are again plastically formed back into a cylindrical shape. This arrangement has the disadvantage that the wire must in each case be plastically deformed for the change of direction. A function check prior to the insertion of the intramedullary nail includes the risk that the wires harden and become brittle through the plastic deformation. An omission of the function check is also not very sensible. Furthermore, the wires must be very precisely guided on all sides within the intramedullary nail in order that no bending takes place.

In an intramedullary nail for the humerus there is the further difficulty that the diameter of the intramedullary chamber is dimensioned to be very small and admits only intramedullary nails with small diameters. Individual guides which completely surround the wire can be manufactured only with a great cost and complexity.

SUMMARY OF THE INVENTION

It is therefore an object of the invention to provide a simply designed intramedullary nail.

This object is satisfied in that the anchoring elements of the nail are combined in a claw of curved wires, with the wires being elastically deformed inside the intramedullary nail in a not outwardly moved state and springing out radially when the claw is axially forwarded so that the anchoring elements can assume their original curved shape.

This arrangement has the advantage that the work for the radial penetration into bone material is already stored with the drawing back of the claw into the shaft of the intramedullary nail. A function check is possible at any time, since the wires are deformed only in the elastic region.

For the individual wire an open, cylindrical guiding groove which guides the wire tip and which is interrupted by a radial aperture is sufficient. For small shaft dimensions the guiding grooves can also be produced by slotting when the tip of the intraniedullary nail can be placed on later. The radial apertures taper in the direction towards the entry tip of the intramedullary nail and center the wires. At the same time a lateral support takes place at the radially emerging wires. A rotational securing already arises at the wire tips through the guiding grooves. In addition cams can be attached to the foot of the claw which run into the guiding grooves as an additional rotational securing. A setting screw is rotatably journalled in the foot of the claw which is however fixed to the claw in the axial direction. Through the combination of the wires in a claw the position of the pre-bent wires relative to one another can be predetermined. Instead of having the planes in which the wires are bent off pass concentrically through the longitudinal axis, more space for the elastic deformation of the wires is won when these planes have a spacing from the longitudinal axis. Transverse bores which lie in the vicinity of the securing head can be applied with an aiming bow in spite of the small diameters for a humerus intramedullary nail since its arm length is dimensioned to be very short. If the setting screw can be introduced from the side of the tip of the intramedullary nail, the hollow intramedullary nail can have a curvature in the region between the setting screw and the securing head. In such a case a flexible screwing tool is required in order to adjust the setting screw. The present intramedullary nail is not restricted to the humerus and can in principle also be used in other tubular bones.

A further improvement, which can be used quite generally for intramedullary nails, consists in designing an intramedullary nail to be elastic in bending in at least one predetermined zone of its shaft in order that it can follow a curvature of the intramedullary nail. In this it is obvious that this zone which is elastic in bending should not lie in the vicinity of a fracture location of a tubular bone. Particular advantages result when this zone which is elastic in bending can also be used as a tension spring, because it is for example formed as a singly or multiply threaded helix, of which the windings have a small predetermined spacing in the tensionless state in such a manner that in a complete compression of this helical spring its windings are only elastically deformed in order to facilitate the hammering in of the intramedullary nail. After the anchoring of a first end of the intramedullary nail a drawing force can be exerted from the opposite end of the intramedullary nail which tensions this helical spring in the drawing direction and then, while maintaining the drawing force at this opposite end of the intramedullary nail, a further anchoring can be applied. The helical spring as a tension spring then exerts a compression on the bone or on an intermediately lying fracture location respectively via the double-ended anchoring of the intramedullary nail, with it not being possible for the compression to diminish so rapidly due to the much weaker spring action of the tension spring in comparison with the rigid intramedullary nail, since a slight change of the spring excursion causes only a slight change of the compression force. The provision of such a zone which is elastic in bending is advantageous in particular everywhere that the anchoring of the two ends of an intramedullary nail can take place independently of the position of these two ends with respect to one another. In a hollow intramedullary nail, such as is shown in the following exemplary embodiments, the anchoring of the two ends of the hollow intramedullary nail is carried out independently of one another from the end of the securing head. The bending and tension spring is therefore cut out of the hollow shaft as a helix in order to allow room on the inner side for a flexible screwdriver. A construction of a complete intramedullary nail with a bending and/or tension spring in a predetermined zone is likewise useful when the anchoring of the two ends takes place independently of their position relative to one another. In patent application WO 98/02104 a complete intramedullary nail which is prolonged by a boring piece is shown, at the two ends of which an aiming device can be placed on independently of one another in order to anchor the respective end. Here as well a zone which is elastic in bending and possibly also elastic in tension and which lies in the central part between the transverse bores has no influence on the approaching of the transverse bores. If such a zone which is elastic in bending and possibly also elastic in tension is planned, bending deflections of more than 2° are useful. In rigid curved intramedullary nails, bending zones with a bending deflection of 4° to 9° are usual. Intramedullary nails which are elastic in bending should also be deflectable in this range. What such a zone which is elastic in bending can look like is described in EP-B-0 614 020 for a flexible screwing tool and can be transferred to an intramedullary nail when the outer diameter of the zone which is elastic in bending is not greater than the outer diameter of the rigid part. In principle all forms of tension springs which are elastic in bending are possible, as long as they do not project beyond the shaft diameter.

In the following the invention will be explained with reference to exemplary embodiments.

BRIEF DESCRIPTION OF THE DRAWINGS

FIG. 1 is a partially sectioned, side view of an intramedullary nail in accordance with the invention;

FIG. 2 shows the inner part of the intramedullary nail of FIG. 1;

FIG. 3 shows the intramedullary nail of FIG. 1 with drawn-in claw;

FIG. 8 shows an intramedullary nail with an aiming bow and with a curvature above the transverse bores; and FIG. 9 shows an intramedullary nail analogous to FIG. 8 in which the curvature is replaced by a zone which is elastic in bending and tension.

DESCRIPTION OF THE PREFERRED EMBODIMENTS

Figure 4:
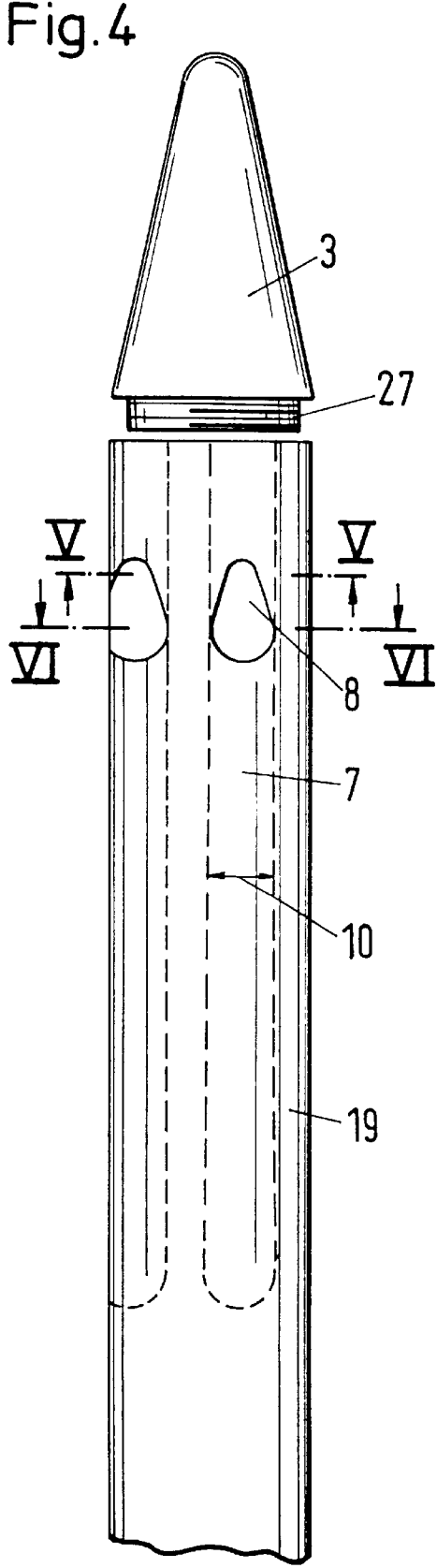
FIG. 4 is an enlarged, fragmentary view of an intramedullary nail in accordance with the invention in the region of the guiding grooves.

An intramedullary nail preferably for the humerus is shown in the figures and comprises a securing head for a hammering-in and aiming device, with the intramedullary nail having at least one transverse bore adjoining at the securing head, and which comprises an entry tip in the vicinity of which anchoring elements can be extended radially. The anchoring elements are combined in a claw of curved wires, with the wires being elastically deformed inside the intramedullary nail in a not outwardly moved state and springing out radially when the claw is axially forwarded so that the anchoring elements can assume their original curved shape.

In the following figures the reference symbols are used uniformly.

In FIGS. 1 and 2 a hollow intramedullary nail has a securing head 1 at which transverse bores 2 adjoin and a shaft 19 with a tip 3 which is subsequently mounted. Below the tip 3 radial apertures 8 are provided, out of which curved wires 6 emerge which are combined in a claw 5.

The wires 6 of the claw 5 are firmly anchored in a foot 13 and are bent off radially in a curvature. A setting screw 14 is rotatably journalled in the foot 13, but is fixed in the axial direction. There is a counter-thread 20 to the setting screw 14 in the shaft 19. The inner part (FIG. 2) is inserted from above when the tip 3 is taken off until the setting screw 14 encounters the thread 20 and is moved further inwards at its inner hexagon 23 with a screwing tool from the opposite side. The claw 5 is drawn into the shaft 19 to such an extent that the wires 6 have completely disappeared and have traveled past the radial apertures 8 with their tips 9. The wires 6 are dimensioned in such a manner that they are deformed only elastically through their stretching. Guiding grooves 7 are attached in the longitudinal direction at the inner side of the shaft 19 which overlap with the apertures 8 and guide the wire tips 9 and secure them against rotation. An additional rotational securing through cams 21 at the foot 13 of the claw is possible if the cams 21 engage into the guiding grooves 7. Through screwing out and in of the setting screw 14 the claw can be moved up and down. As soon as the claw tips 9 coming from below reach the apertures 8, they spring radially outwards and bore into a tubular bone surrounding them if the intramedullary nail is hammered in into the latter. Through a continuation of the axial movement the extended part is completely freed for the automatic curving.

Figure 5:
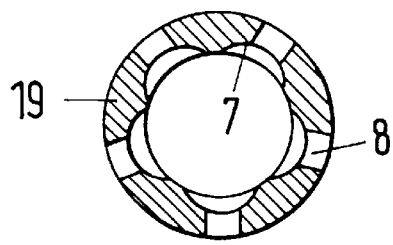
FIG. 5 is a cross-sectional view of the upper region of the radial apertures of FIG. 4.

The construction will be explained more precisely using FIGS. 4, 5 and 6 as examples. The shaft 19 of the intramedullary nail has an outer diameter of 6 mm and consists of a metal tube, for example steel or titanium, onto which a tip 3 with a thread 27 can be screwed on. Five guiding grooves 7 with as great a width 10 as possible are struck on the inner side of this tube in order to guide the tips 9 of the claw 5 and to keep it elastically deformed. The wires 6 of the claw 5 are led out of the foot 13 at first cylindrically and parallel to the longitudinal axis 12 and are curved radially outwardly by about 90° in the tensionless state with a radius of curvature of 8 mm. During the assembly of the claw 5 the claw tips 9 are compulsorily drawn into the guiding grooves 7 and elastically subjected to a bias force. Due to the curvature of the wires 6 the claw 5 with its tips 9 can travel past the radial apertures 8 on the way towards the inside. If however the claw is displaced outwardly, then the tips 9, which are subjected to a bias force, are compulsorily captured by the apertures 8, which have a greatest width 10 of the guiding grooves 7, and—because the apertures 8 taper in the direction towards the tip 3 of the intramedullary nail—are centered and laterally supported. In this the wires 6 move radially outwardly to the extent to which they are released in the axial direction.

Figure 6:
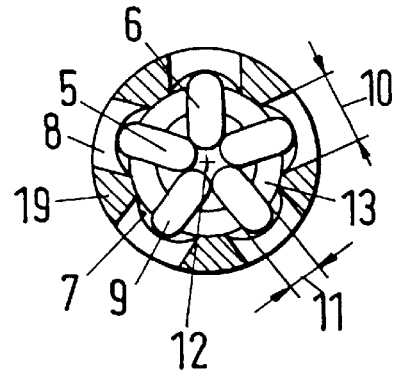
FIG. 6 is a cross-sectional view of the lower region of the radial apertures of FIG. 4.

In FIG. 6 one recognizes that the planes of the wire curvature are directed concentrically to longitudinal axis 12 and admit relatively little space for the extension of the wires.

Figure 7:
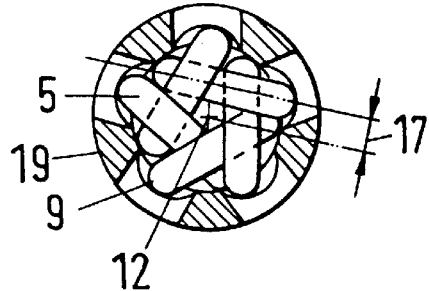
FIG. 7 is a cross-sectional view showing an arrangement as in FIG. 6 in which the wires with their planes of curvature have a spacing from the longitudinal axis.

In FIG. 7, therefore, an arrangement is shown in which the planes of the wire curvature extend past the longitudinal axis at a distance 17 from the longitudinal axis 12 and make a substantially larger space in the extension of the wires 6 available. The wire may in this case be thicker and stiffer than in FIG. 6 and is still deformed in its elastic region. Since the wire guides itself only with its tip 9, it can be moved out with its cylindrical part, which is supported in the foot 13, to such an extent that a part of the curvature is taken up in the drawn-in wire through curvature of the cylindrical part in the opposite direction (see FIG. 3). The extended wire 6' then receives an S-shaped curvature.

In FIG. 8 the shaft 19 of the intramedullary nail widens to a securing head 1. A hammering-in and aiming device which can be pushed on in a predetermined position is screwed on with a hollow securing screw 25 at the head 1 and enables transverse bores 2 in the hammered-in shaft 19 to be found via an aiming bow 26 which is guided parallel to the shaft and to be provided with anchoring screws in order to achieve a second anchoring at the securing head 1 in addition to the anchoring through the claw 5 at the tip 3 of the intramedullary nail. In this the intramedullary nail may also have a slight curvature 22 to the longitudinal axis 12 of the securing head 1 if the screwdriver for the setting screw 14 of the inner part (FIG. 2) is flexible in the bending direction. The implanted intramedullary nail receives a closure cap (not shown here) which keeps the inner space free from ingrowing tissue. Likewise the transverse bores 2 are largely closed off by bone screws. For removing the intramedullary nail the closure cap and the bone screws in the transverse bores must be removed. Then a screwing tool can be introduced in the inner hexagon 23 (FIG. 2) in order to draw back the claw 5 into the intramedullary nail. Following this a sliding hammer (not shown here) can be screwed on at the securing head in order to hammer out the intramedullary nail.

In FIG. 9 the hollow shaft 19 is provided with a zone 28 which is elastic in bending and tension through a groove in the form of a helix. A groove of this kind can be produced through water jet cutting, spark erosive wire cutting, laser processing or hob cutting with a disc milling tool. The intramedullary nail is hammered in with a hammering-in and aiming device in accordance with FIG. 8 and assumes the curvature of the intramedullary chamber. In a next step the claw S is moved out with a flexible screwdriver and anchored in the bone. In a further step the securing head 1 with the foot of the aiming device is drawn out on the insertion side to such an extent relative to the bone that a predetermined drawing tension arises at the elastic zone 28. This position is held until prolongations of the transverse bores 2 are bored in the bone material with the aiming bow and bone screws are screwed in for anchoring the end with the securing head 1.

What is claimed is:

1. Intramedullary nail comprising an elongate body defining a cavity and having a securing head proximate one end of the body for a hammering-in and aiming device, at least one transverse bore adjoining at the securing head, and an entry tip at another end of the body, anchoring elements which can be extended radially in the vicinity of the entry tip, the anchoring elements being combined in a claw of curved wires, with the wires being elastically deformed inside the cavity in a not outwardly moved state and springing out radially when the claw is axially forwarded towards the tip so that the anchoring elements can assume their original curved shape, and guiding grooves at the inner side of the cavity which extend in the longitudinal direction and which in each case have a radial aperture in order to guide tips of the deformed wires up to their radial emergence.

2. Intramedullary nail in accordance with claim 1 wherein the apertures have the width of the guiding groove and taper in the direction of the entry tip down to the width of a wire in order to give the axially forwarded and radially emergent wires support in the axial direction and against a rotation about the longitudinal axis.

3. Intramedullary nail in accordance with claim 1 wherein the claw has a foot, and including a setting screw coupled to the foot for moving the foot and the claw axially.

4. Intramedullary nail in accordance with claim 1 including means securing the claw against rotation relative to the elongate body.

5. Intramedullary nail in accordance with claim 1 wherein the claw comprises at least three curved wires.

6. Intramedullary nail in accordance with claim 1 wherein the wires have curvatures that extend in planes which are arranged parallel to and at a distance from a longitudinal axis of the elongate body.

7. Intramedullary nail in accordance with claim 1 consisting of metal.

8. Intramedullary nail in accordance with claim 7 wherein the metal comprises one of titanium and an alloy of titanium.

9. Intramedullary nail in accordance with claim 1 including an aiming bow for transverse bores that can be attached to the securing head.

10. Intramedullary nail in accordance with claim 1 wherein the elongate body has a curvature in the longitudinal direction.

11. Intramedullary nail in accordance with claim 1 wherein the elongate body can be bent elastically by an angle greater than 2° in a predetermined zone.

12. Intramedullary nail in accordance with claim 11 wherein the predetermined zone is formed as a threaded helix which can be used as a tension spring for maintaining a compression force.

13. Intramedullary nail comprising an elongate body defining a cavity and having a securing head proximate one end of the body for a hammering-in and aiming device, at least one transverse bore adjoining at the securing head, and an entry tip at another end of the body, the elongate body being elastically bendable by an angle greater than 2° in a predetermined zone, and anchoring elements which can be extended radially in the vicinity of the entry tip, the anchoring elements being combined in a claw of curved wires, with the wires being elastically deformed inside the cavity in a not outwardly moved state and springing out radially when the claw is axially forwarded towards the tip so that the anchoring elements can assume their original curved shape.

* * * * *